United States Patent
Wu et al.

(10) Patent No.: US 9,012,147 B2
(45) Date of Patent: Apr. 21, 2015

(54) METHOD OF ENZYMATIC GENE CHIP DETECTION KIT

(71) Applicants: CaryGene Biotechnology Corp., Kaohsiung (TW); Fooyin University Hospital, Pingtung County (TW)

(72) Inventors: Chan-Han Wu, Kaohsiung (TW); Shiu-Ru Lin, Kaohsiung (TW); Hsueh-Chiao Liu, Kaohsiung (TW)

(73) Assignees: CaryGene Biotechnology Corp., Kaohsiung (TW); Fooyin University Hospital, Pingtung County (TW)

( * ) Notice: Subject to any disclaimer, the term of this patent is extended or adjusted under 35 U.S.C. 154(b) by 64 days.

(21) Appl. No.: 13/906,890

(22) Filed: May 31, 2013

(65) Prior Publication Data

US 2014/0147841 A1     May 29, 2014

(30) Foreign Application Priority Data

Nov. 28, 2012    (TW) .............................. 101144416 A

(51) Int. Cl.
      *C12Q 1/68*        (2006.01)

(52) U.S. Cl.
      CPC ................ *C12Q 1/6806* (2013.01); *C12Q 1/68* (2013.01)

(58) Field of Classification Search
      CPC ........................................................ C12Q 1/68
      USPC ........................................................ 435/6.1
      See application file for complete search history.

*Primary Examiner* — Ardin Marschel

(74) *Attorney, Agent, or Firm* — Jackson IPG PLLC; Demian K. Jackson

(57) ABSTRACT

A gene chip is provided for detection. When used on clinical detection, the gene chip directly detects blood without magnification. Gene expressions are examined with high sensitivity and convenience simultaneously.

20 Claims, 1 Drawing Sheet

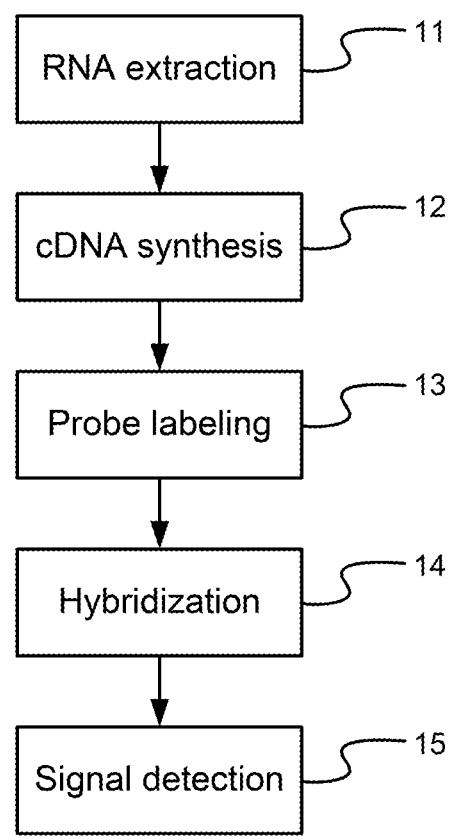

METHOD OF ENZYMATIC GENE CHIP DETECTION KIT

TECHNICAL FIELD OF THE INVENTION

The present invention relates to detection with a gene chip; more particularly, relates to using a gene chip having 17 agents for clinical direct detection on blood without magnification.

DESCRIPTION OF THE RELATED ARTS

Analysis on gene overexpression improves clinical diagnosis. Related technologies includes northern blotting, reverse transcription polymerase chain reaction (RT-PCR) and real-time PCR. However, northern blotting requires a complex procedure and a lot of samples, which applied in study only and not for clinical use. RT-PCR and real-time PCR are simpler yet still have some problems. First problem is pollution which caused false positive on detection. Second one is related to RT-PCR, where, on comparing different samples, it is hard to control efficiency of sequence magnification. Third one is interference on annearling between primers, where, on detecting gene groups, PCR-related technologies will take time, become complex and cost high.

A prior art uses a nylon membrane array for cancer detection. An expression of multi-mRNA labeled object in peripheral blood is obtained. The expression level of the molecular label are evaluated through RT-PCR and the nylon membrane. Data are obtained from RT-PCR and the nylon membrane, which is limited by linear regression analysis. Results from these two origins show high co-relationship ($r=0.979$, $P<0.0001$). Another prior art is a gene chip of weighted chemiluminescent membrane array (WCHMA). Abnormal situation of target K-ras over a target therapeutic drug for a lung cancer patient is analyzed.

Although applications of nylon membrane gene chips for molecular diagnosis and drug evaluation are revealed, detection specificity is hard to improve since every gene is deemed equally important to a specific disease. Another prior art detects and analyzes mass samples rapidly, yet magnification is required beforehand. Direct detection on blood to observe gene expressions with a gene chip is still not available.

Hence, the prior arts do not fulfill all users' requests on actual use.

SUMMARY OF THE INVENTION

The main purpose of the present invention is to use a gene chip for clinical direct detection on blood without magnification to provide high sensitivity and convenience at the same time.

To achieve the above purpose, the present invention is a method of an enzymatic gene chip detection kit, comprising steps of:

(a) evenly mixing a sample, a protease solution and a lysis solution to be reacted at a temperature of 45~67 Celsius degrees (° C.) for 8~12 minutes (min); adding a magnetic bead solution and a binding solution to be evenly mixed in to be reacted at a temperature of 20~30° C. for 8~12 min; fixing magnetic beads in the magnetic bead solution with a magnet to remove a reacting solution thus obtained; adding a washing solution to be evenly mixed in; fixing magnetic beads with a magnet to remove a reacting solution thus obtained; adding an elution solution to be evenly mixed in to be reacted at a temperature of 56~84° C. for 8~12 min; fixing magnetic beads with a magnet to obtain an RNA solution;

(b) processing reaction to the RNA solution at a temperature of 56~84° C. for 8~12 min; adding a primer solution to be evenly mixed in to be reacted at a temperature of −0.5~0.5° C. for 1.5~2.5 min; adding a reverse transcription solution and a reverse transcriptase solution to be evenly mixed in to be reacted at a temperature of 34~50° C. for 96~144 min to obtain a cDNA solution;

(c) processing reaction to the cDNA solution at a temperature of 76~114° C. for 4~6 min; lowering a temperature to −0.5~0.5° C. to process reaction for 1.5~2.5 min; adding a labeling solution to be evenly mixed in to be reacted at a temperature of 34~50° C. for 192~288 min to obtain a probe solution;

(d) putting a gene chip in a reaction chamber; adding a hybridization solution to be evenly mixed in to be reacted at a temperature of 34~50° C. for 8~12 min; processing reaction to the probe solution at a temperature of 76~114° C. for 4~6 min; lowering a temperature of the probe solution to −0.5~0.5° C. to be reacted for 1.5~2.5 min; adding the probe solution into the reaction chamber to be reacted at a temperature of 34~50° C. for 384~576 min to obtain a hybridization solution, where an oligonucleotide segment is selected; the oligonucleotide segment comprises a plurality of target genes; two housekeeping genes are obtained to control reaction quality; the housekeeping genes fixes the oligonucleotide segment on the gene chip to obtain a specific sequence covered on the gene chip; and (e) removing the hybridization solution to leave the gene chip in the reaction chamber; adding a first washing solution to be removed after 4~6 min; adding the first washing solution to be removed after 4~6 min again; adding a second washing solution at a temperature of 34~50° C. to be removed after 4~6 min; adding the second washing solution at the temperature of 34~50° C. to be removed after 4~6 min again; adding a blocking solution to be reacted for 24~36 min and removed; adding an antibody solution to be reacted for 72~108 min and removed; adding a third washing solution to be reacted for 4~6 min and removed; adding a third washing solution to be reacted for 4~6 min and removed again; adding a chromogen solution to be reacted at a temperature of 34~50° C. to obtain signals; adding water to wash until signals stop; and drying the gene chip to obtain a final result.

Accordingly, a novel method of an enzymatic gene chip detection kit is obtained.

BRIEF DESCRIPTIONS OF THE DRAWINGS

The present invention will be better understood from the following detailed description of the preferred embodiment according to the present invention, taken in conjunction with the accompanying drawing, in which FIG. 1 is the flow view showing the preferred embodiment according to the present invention.

DESCRIPTION OF THE PREFERRED EMBODIMENT

The following description of the preferred embodiment is provided to understand the features and the structures of the present invention.

Please refer to FIG. 1, which is a flow view showing a preferred embodiment according to the present invention. As shown in the figure, the present invention is a method of an enzymatic gene chip detection kit. The present invention uses an enzymatic gene chip detection kit, comprising a gene chip and a set of gene chip reagents. The gene chip has two housekeeping genes for controlling quality of reactions of the gene chip. The set of gene chip reagents comprises all reagents required in a flow of the reactions of the gene chip. The flow of the reactions of the gene chip comprises RNA extraction, cDNA synthesis, probe labeling, hybridization and signal detection. The gene chip requires 17 reagents for the reactions. After the reactions, expressions of the housekeeping genes are observed. The present invention comprises the following steps:

(a) RNA extraction 11: A sample is evenly mixed with 6 mAU of a protease K solution. Then, a lysis solution is added to be evenly mixed in. The lysis solution comprises 200 millimoles (mM) of 4-(2-hydroxyethyl)-1-piperazineethanesulfonic acid, 400 mM of sodium chloride (NaCl) and 1% of octyl phenoxy polyethoxy (Triton X-100). After the mixed solution is reacted at a temperature of 56 Celsius degrees (° C.) for 10 minutes (min), a magnetic bead solution is added to be evenly mixed in, which is a solution of 25 mg/ml of hydroxyl-silicon dioxide magnetic bead. Then, the mixed solution is evenly mixed with a binding solution consisting 12.5% of polyethylene glycol (PEG) and 2 moles (M) of NaCl. After the mixed solution is reacted at a temperature of 25° C. for 10 min, magnetic beads in the magnetic bead solution are fixed by a magnet for removing a reacting solution thus obtained. A washing solution, consisting 70% of ethanol, 1% of glycerin and 100mM of ammonium acetate, is evenly mixed in. The magnetic beads are fixed by a magnet again for removing a reacting solution thus obtained. An elution solution, consisting 20 mM of tris-hydrogen chloride (Tris-HCl) and 1 mM of ethylenediaminetetraacetic acid (EDTA), is evenly mixed in. After the mixed solution is reacted at a temperature of 70° C. for 10 min, the magnetic beads are fixed by a magnet for collecting an RNA solution thus obtained.

(b) cDNA synthesis 12: After putting the RNA solution for reaction at a temperature of 70° C. for 10 min, a primer solution, consisting 300 nanograms per microliter (ng/ul) of oligo-dT primer and 100 ng/ul of random primer, is evenly mixed in. After putting the mixed solution for reaction at a temperature of 0° C. for 2 min, a reverse transcription solution, consisting 250 mM of Tris-HCl, 375 mM of potassium chloride (KCl), 15 mM of magnesium chloride (MgCl) and 100 mM of dithiothreitol (DTT), is evenly mixed in. Then, a reverse transcriptase solution, consisting 200 units of reverse transcriptase MLV and 25 units of ribonuclease inhibitor (RNases inhibitor), is evenly mixed in. After putting the mixed solution for reaction at a temperature of 42° C. for 120 min, a cDNA solution is obtained.

(c) Probe labeling 13: After putting the cDNA solution for reaction at a temperature of 95° C. for 5 min, the cDNA solution is reacted at a temperature of 0° C. for 2 min and, then, is added with a labeling solution evenly mixed in, where the labeling solution comprises 80 nanograms per milliliter (ng/ml) of random primer, 2 units per microliter (U/ul) of Klen Taq polymerase, 1 mM of deoxyadenosine triphosphate (dATP), 1 mM of deoxycytidine triphosphate (dCTP), 1 mM of deoxyguanosine triphosphate (dGTP), 0.6 mM of deoxythymidine triphosphate (dTTP), 0.4 mM of biotin-deoxyuridine triphosphate (biotin-dUTP), 20% of Klen Taq buffer and 20% of glycerin. After putting the mixed solution for reaction at a temperature of 42° C. for 240 min, a probe solution is obtained.

(d) Hybridization 14: A gene chip is put into a reaction chamber. A hybridization solution, consisting 10% of polyethylene glycol (PEG), 10% of sodium dodecyl sulfate (SDS) and 2 moles (M) of sodium chloride (NaCl), is evenly mixed in. The probe solution is reacted at a temperature of 95° C. for 5 min and continuous reaction at a temperature of 0° C. for 2 min. After putting the mixed solution for reaction at a temperature of 42° C. for 10 min, the probe solution is added into the reaction chamber. After putting the mixed solution for reaction at a temperature of 42° C. for 480 min, a hybridization solution is obtained.

(e) Signal detection 15: The hybridization solution is removed to leave the gene chip in the reaction chamber. A first washing solution, consisting 0.5% of SDS and 0.5× of saline sodium citrate (SSC), is added and is removed after 5 min of reaction. In the same way, the first washing solution and is added and is removed again. A second washing solution of 2× of SSC is added and is removed after 5 min of reaction at a temperature of 42° C. In the same way, the second washing solution is added and is removed again. A filling solution, consisting 1.5% of blocking buffer, is added and removed after 30 min of reaction. An antibody solution, consisting 0.7 ug/ml of alkaline phosphatase-conjugated IgG anti-biotin, is added and removed after 90 min of reaction. A third washing solution, consisting 1% of SDS, 1% of octyl phenoxy polyethoxy and 1% of glycerin, is added and removed after 5 min of reaction. In the same way, the third washing solution is added and is removed again. A chromogen solution, consisting 1× of 5-bromo-4-chloro-3-indolyl-phosphate/p-nitroblue tetrazolium chloride (BCIP/NBT), is added for reaction at a temperature of 42° C. until signals are generated. Then, water is added for washing until signals stop generating. A detection result is finally obtained after drying.

In step (d), the gene chip is a material coated with a nylon membrane or a thermoplastic composite; the thermoplastic composite can be polypropylene (PP) or polymethyl methacrylate (PMMA). Regarding the gene chip, an oligonucleotide segment is selected; the oligonucleotide segment comprises a plurality of target genes; two housekeeping genes are used to control reaction quality; and, the housekeeping genes fixes the oligonucleotide segment on the gene chip to form a specific sequence covered on the gene chip. Therein, the oligonucleotide segment is a synthetic oligonucleotide consisting in a solution; the solution has a density of 10~200 mM; the oligonucleotide segment has a length of 40~60 bases; specific sequence of each of the target genes are complement to the those of the other target genes; more than 30 normal liters (NL) of the solution of synthetic oligonucleotide is distributed on the gene chip to duplicate and arrange the oligonucleotide segment in a planned way; and, after being dried, the oligonucleotide segment is radiated by ultraviolet (UV) to be solidified. Thus, a gene chip is fabricated according to the present invention.

Hence, the present invention can be used in clinical tests, where direct test on blood is possible without magnification. With the gene chip, gene expressions in the blood are observed with high sensitivity and convenience.

To sum up, the present invention is a method of an enzymatic gene chip detection kit, where direct test on blood is possible without magnification; and, with a gene chip fabricated according to the present invention, gene expressions in the blood are observed with high sensitivity and convenience.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of an enzymatic gene chip detection kit, comprising steps of:
  (a) evenly mixing a sample, a protease solution and a lysis solution to be reacted at a temperature of 45~67 Celsius degrees (° C.) for 8-12 minutes (min); adding a magnetic bead solution and a binding solution to be evenly mixed in to be reacted at a temperature of 20~30° C. for 8~12 min; fixing magnetic beads in said magnetic bead solution with a magnet to remove a reacting solution thus obtained; adding a washing solution to be evenly mixed in; fixing magnetic beads with a magnet to remove a reacting solution thus obtained; adding an elution solution to be evenly mixed in to be reacted at a temperature of 56~84° C. for 8~12 min; fixing magnetic beads with a magnet to obtain an RNA solution;

(b) processing reaction to said RNA solution at a temperature of 56~84° C. for 8~12 min; adding a primer solution to be evenly mixed in to be reacted at a temperature of −0.5~0.5° C. for 1.5~2.5 min; adding a reverse transcription solution and a reverse transcriptase solution to be evenly mixed in to be reacted at a temperature of 34~50° C. for 96~144 min to obtain a cDNA solution;

(c) processing reaction to said cDNA solution at a temperature of 76~114° C. for 4~6 min; lowering a temperature to −0.5~0.5° C. to process reaction for 1.5~2.5 min; adding a labeling solution to be evenly mixed in to be reacted at a temperature of 34~50° C. for 192~288 min to obtain a probe solution;

(d) putting a gene chip in a reaction chamber; adding a hybridization solution to be evenly mixed in to be reacted at a temperature of 34~50° C. for 8~12 min; processing reaction to said probe solution at a temperature of 76~114° C. for 4~6 min; lowering a temperature of said probe solution to −0.5~0.5° C. to be reacted for 1.5~2.5 min; adding said probe solution into said reaction chamber to be reacted at a temperature of 34~50° C. for 384~576 min to obtain a hybridization solution, wherein an oligonucleotide segment is selected; said oligonucleotide segment comprises a plurality of target genes; two housekeeping genes are obtained to control reaction quality; said housekeeping genes fixes said oligonucleotide segment on said gene chip to obtain a specific sequence covered on said gene chip; and (e) removing said hybridization solution to leave said gene chip in said reaction chamber; adding a first washing solution to be removed after 4~6 min; adding said first washing solution to be removed after 4~6 min again; adding a second washing solution at a temperature of 34~50° C. to be removed after 4~6 min; adding said second washing solution at said temperature of 34~50° C. to be removed after 4~6 min again; adding a blocking solution to be reacted for 24~36 min and removed; adding an antibody solution to be reacted for 72~108 min and removed; adding a third washing solution to be reacted for 4~6 min and removed; adding said third washing solution to be reacted for 4~6 min and removed again; adding a chromogen solution to be reacted at a temperature of 34~50° C. to obtain signals; adding water to wash until signals stop; and drying said gene chip to obtain a final result.

2. The method according to claim 1,
wherein said gene chip is selected from a group consisting of a nylon membrane and a thermoplastic composite and said thermoplastic composite is selected from a group consisting of polypropylene (PP) and polymethyl methacrylate (PMMA).

3. The method according to claim 1,
wherein said oligonucleotide segment is a synthetic oligonucleotide consisting in a solution and said solution has a density of 10~200 millimoles (mM);
wherein said oligonucleotide segment has a length of 40~60 bases and specific sequences of each of said target genes are complement to said specific sequences of the other target genes;
wherein more than 30 normal liters (NL) of said solution of synthetic oligonucleotide is distributed on said gene chip to duplicate and arrange said oligonucleotide segment and, after being dried, to be radiated by ultraviolet (UV) to be solidified.

4. The method according to claim 1,
wherein, in step (a), said protease solution is a solution of protease K.

5. The method according to claim 1,
wherein, in step (a), said lysis solution is a solution of 4-(2-hydroxyethyl)-1-piperazineethanesulfonic acid, sodium chloride (NaCl) and octyl phenoxy polyethoxy (Triton X-100).

6. The method according to claim 1,
wherein, in step (a), said magnetic bead solution is a solution of hydroxyl-silicon dioxide magnetic bead.

7. The method according to claim 1,
wherein, in step (a), said binding solution is a solution of polyethylene glycol (PEG) and NaCl.

8. The method according to claim 1,
wherein, in step (a), said washing solution is a solution of ethanol, glycerin and ammonium acetate.

9. The method according to claim 1,
wherein said elution solution is a solution of tris-hydrogen chloride (Tris-HCl) and ethylenediaminetetraacetic acid (EDTA).

10. The method according to claim 1,
wherein, in step (a), said primer solution is a solution of oligo-dT primer and random primer.

11. The method according to claim 1,
wherein, in step (b), said reverse transcription solution is a solution of Tris-HCl, potassium chloride (KCl), magnesium chloride (MgCl) and dithiothreitol (DTT).

12. The method according to claim 1,
wherein, in step (b), said reverse transcriptase solution is a solution of reverse transcriptase (MMLV) and ribonuclease inhibitor (RNases inhibitor).

13. The method according to claim 1,
wherein, in step (c), said labeling solution is a solution of random primer, Klen Taq polymerase, deoxyadenosine triphosphate (dATP), deoxycytidine triphosphate (dCTP), deoxyguanosine triphosphate (dGTP), deoxythymidine triphosphate (dTTP), biotin-deoxyuridine triphosphate (biotin-dUTP), Klen Taq buffer and glycerin.

14. The method according to claim 1,
wherein, in step (d), said hybridization solution is a solution of PEG, sodium dodecyl sulfate (SDS) and NaCl.

15. The method according to claim 1,
wherein, in step (e), said first washing solution is a solution of SDS and saline sodium citrate (SSC).

16. The method according to claim 1,
wherein, in step (e), said second washing solution is a solution of sodium citrate.

17. The method according to claim 1,
wherein, in step (e), said third washing solution is a solution of SDS, octyl phenoxy polyethoxy and glycerin.

18. The method according to claim 1,
wherein, in step (e), said filling solution is a solution of blocking buffer.

19. The method according to claim 1,
wherein, in step (e), said antibody solution is a solution of alkaline phosphatase-conjugated IgG anti-biotin.

20. The method according to claim 1, wherein, in step (e), said chromogen solution is a solution of 5-Bromo-4-chloro-3-indolyl phosphate/p-nitro-blue tetrazolium chloride (BCIP/NBT).

* * * * *